Figure 1:
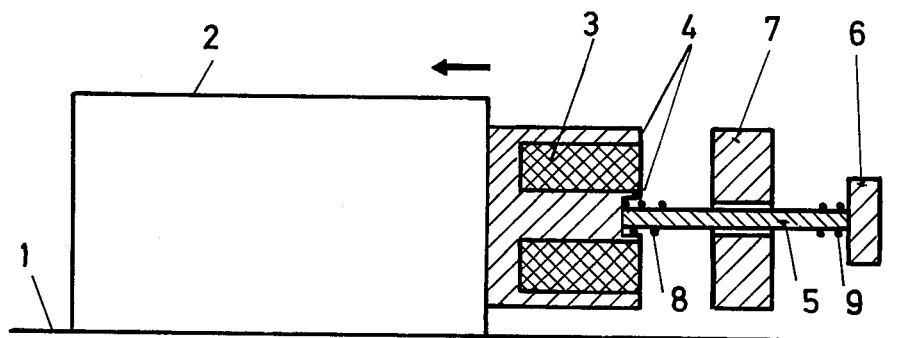

United States Patent
Soderqvist

[11] 3,957,162
[45] May 18, 1976

[54] METHOD AND DEVICE FOR DISPLACEMENT OF A WORKPIECE

[75] Inventor: Anton L. O. Söderqvist, Vallingby, Sweden

[73] Assignee: LKB-Produkter AB, Bromma, Sweden

[22] Filed: Apr. 5, 1974

[21] Appl. No.: 458,404

[30] Foreign Application Priority Data
Apr. 6, 1973 Sweden............................ 7304862

[52] U.S. Cl. ............................ 214/1 R; 180/7 R; 214/152; 310/26
[51] Int. Cl.² ............................................ B65G 35/00
[58] Field of Search ................ 214/1 R, 1.1–1.7, 214/152; 254/105; 180/7 R; 29/200 P; 60/721; 310/26

[56] References Cited
UNITED STATES PATENTS

| | | | |
|---|---|---|---|
| 1,743,978 | 1/1930 | Quisling | 115/.5 R |
| 2,496,051 | 1/1950 | Hillier | 214/1 R X |
| 3,138,749 | 6/1964 | Stibitz | 214/1 R X |
| 3,266,233 | 8/1966 | Farrall | 180/7 R X |
| 3,377,489 | 4/1968 | Brisbane | 214/1 R X |
| 3,525,140 | 8/1970 | Cachon et al. | 29/200 P |

FOREIGN PATENTS OR APPLICATIONS

| | | | |
|---|---|---|---|
| 1,906,960 | 8/1970 | Germany | 180/7 R |

*Primary Examiner*—Frank E. Werner

[57] ABSTRACT

The present invention relates to the displacement of a workpiece in a given direction to a good accuracy. According to the invention the friction between the workpiece and a sliding surface on which the workpiece is resting is overcome by a mechanical impulse. Preferably, the mechanical impulse is accomplished by means of an electrical voltage pulse, by mechanical or piezoelectrical means.

23 Claims, 7 Drawing Figures

METHOD AND DEVICE FOR DISPLACEMENT OF A WORKPIECE

The present invention relates to a method and a device for displacement in a given direction of a workpiece, resting on a sliding surface.

Within technology there is often a problem to accomplish a displacement of a workpiece with very good precision. The displacement referred to herein can be several centimeters or parts of millimeters, occasionally varying within this range for one and the same workpiece and with unchanged requirements of precision. The term workpiece is in the following directed towards an object which permanently or for some working purpose shall be applied in an accurately determined position, as well as towards a tool for performing a work operation in an accurately determined position as well as towards attachments and working tables for such objects and tools.

An example of such a displacement where good precision is required is the adjustment of the knife table of an ultramicrotome. At sectioning of an object in an ultramicrotome usually the knife is stationary while the object is situated on a specimen arm, which is conveyed towards the knife edge. It is then necessary, that the knife exhibits adjustment possibilities to provide for the best sectioning. This is practically solved in this way that the knife is attached to a knife table, which is displacable in several directions. This displacement to the best knife position should be accomplished with very good precision.

Another example of the need for displacements for very short distances with great accuracy is at welding of electrodes in the manufacture of microcircuits, at which a very accurate fitting-in has to be achieved.

At work with fine mechanics in general there is often a need for displacements for short distances with good accuracy.

The method, mainly utilized at the very small displacement, necessary at these and other applications, is displacement by micrometer screw. With a sufficiently small pitch of thread and possibly changing of the rotation moment, very small and accurate displacements can be achieved.

Displacement by micrometer screw is however mainly performed manually. However, this is a disadvantage in many connections, where remote control is required, for instance at work in cold or at risk of radiation. Furthermore, the micrometer screw has to be heated to be able to work in cold.

The possibility to govern the displacement electrically at automated, programmed manufacturing operations is also an advantage.

A device for displacement by a micrometer screw, of course, can be provided by an electric motor, but this apparatus comprising the necessary gear changes will be expensive, if high accuracy should be achieved at the displacement.

It is a purpose of the present invention to provide a method and a device for displacement of a workpiece to a very high accuracy, in which the displacement is accomplished electrically.

It is also a purpose of the present invention to provide a method and a device by means of which displacement of a workpiece can be achieved to a very good accuracy, in which the displacement is remotely governed electrically.

It is also a purpose of the present invention to provide a method and a device by means of which very small displacements can be obtained.

It is also a purpose of the present invention to provide a device to accomplish very small displacements to a very good accuracy, the device being relatively simple and cheap to produce.

The characteristics of the invention are obvious from the claims following the specification.

The invention will now be further explained with reference to the attached drawings, on which FIGS. 1 – 6 are showing various embodiments of the device according to the invention.

Figure 2:
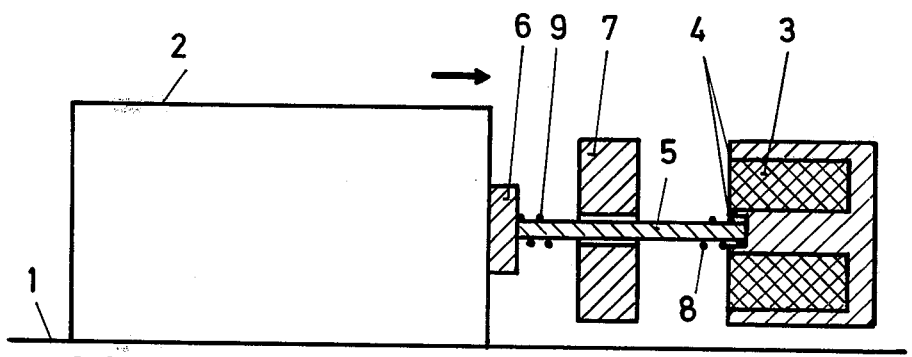

In FIGS. 1 and 2 is denoted by 1 a sliding surface on which a workpiece 2 can be displaced, 3 denotes an electromagnet having magnet poles 4. 5 denotes a guide dowel, which is provided with a stop 6. On the guide dowel 5 a magnet keeper 7 is slidably lodged. At the attachment of the guide dowel 5 at the electromagnet 3 a first resilient element 8 is applied. At the stop 6 a second resilient element 9 is situated.

Figure 3:
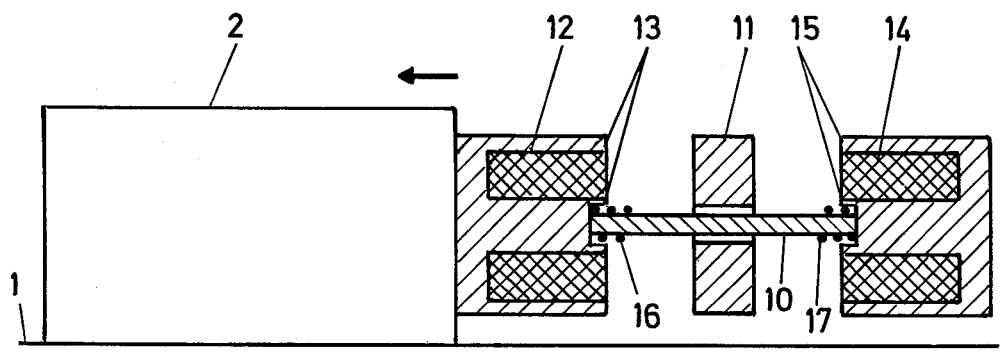

In FIG. 3 is denoted by 10 a guide dowel on which a magnet keeper 11 is slidably lodged. 12 denotes a first electromagnet, having magnet poles 13. 14 denotes a second electromagnet, having magnet poles 15. 16 and 17 are directed towards first and second resilient elements, respectively.

Figure 4:
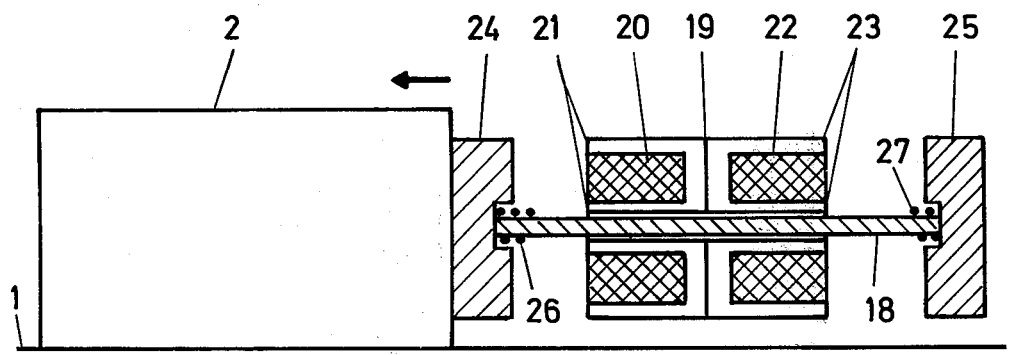

In FIG. 4, 18 denotes a guide dowel on which a magnet casing 19 is slidably lodged. The magnet casing contains a first electromagnet 20, having magnet poles 21, and a second electromagnet 22, having magnet poles 23. 24 and 25 denote first and second stationary magnet keepers, respectively, 26 and 27 first and second resilient elements, respectively.

Figure 5A:
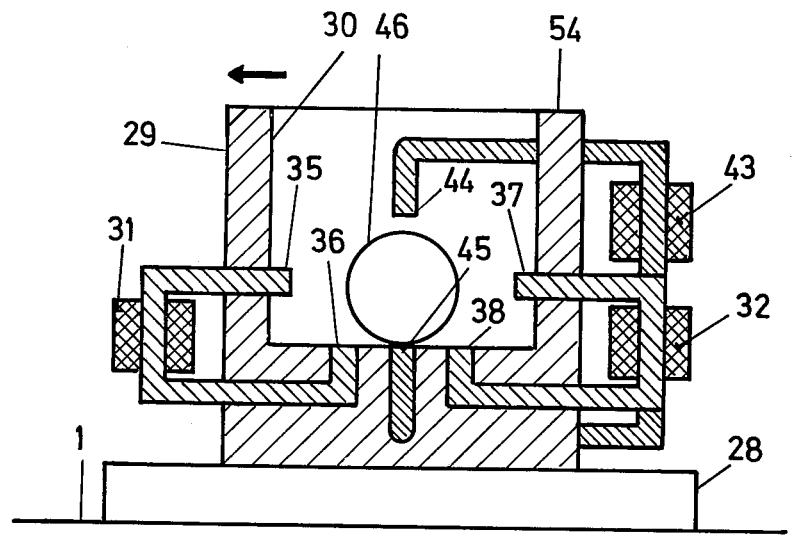
Figure 5B:
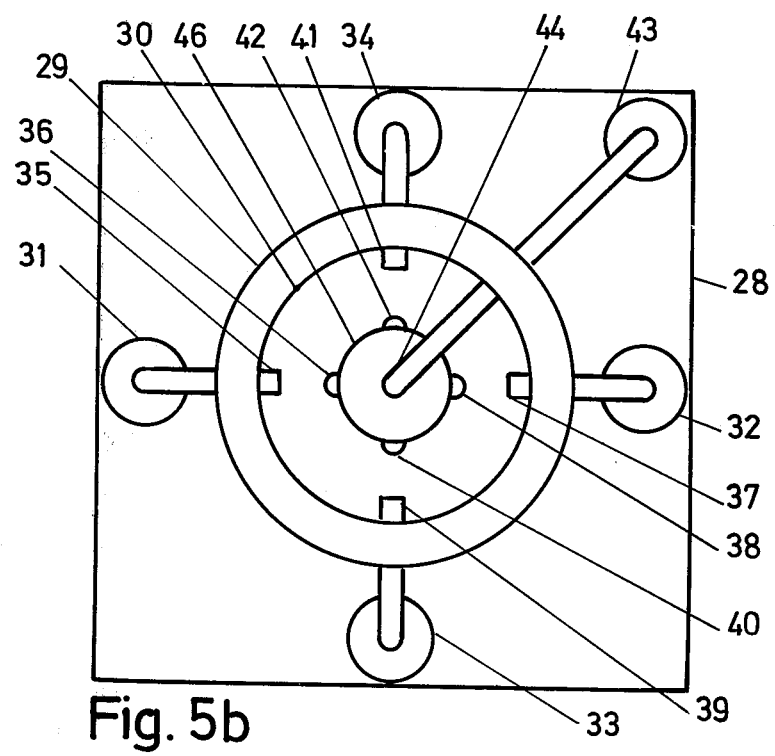

In FIGS. 5a and 5b, 28 denotes a base plate forming part of the workpiece, 29 a cylindrical part of the workpiece, exhibiting a cylindrical recess 30 and an annular upper surface 54.

31, 32, 33, 34 denote first, second, third, and fourth electromagnets, respectively symmetrically situated around the cylinder 29, and having magnet poles 35, 36, and 37, 38 and 39, 40 and 41, 42, respectively, which are led through the wall of the workpiece to the recess. 43 denotes a fifth electromagnet having magnet poles 44 and 45. A magnet keeper being a sphere is denoted by 46.

The electromagnets in FIGS. 1-5 are connected to voltage sources, not shown in the figures.

Figure 6:
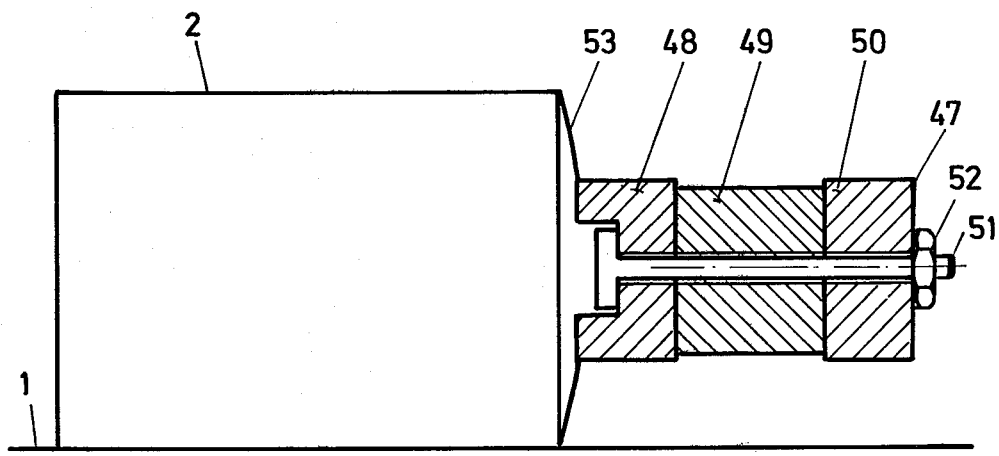

In FIG. 6 is denoted by 47 a piezoelectrical transducer comprising a first block 48, a piezoelectrical element 49 and a second block 50, which are kept together by a bolt 51 with nut 52. The piezoelectrical transducer is attached to the workpiece 2 by a plate spring 53. The piezoelectrical element 49 is connected to a voltage source, not shown in the figure.

The device shown in FIG. 1 is working in the following way. The sliding surface 1 and the bottom surface of the workpiece 2 are suitably carefully face-ground, in order that reproducible frictional conditions are at hand between workpiece and sliding surface. At displacement, the electromagnet 3 is given a well adapted voltage pulse from a voltage source, not shown in the figure, which will bring about attraction of the magnet keeper 7 against the poles 4 of the electromagnet. The magnet keeper will hit the magnet poles 4 with an impact, which to the electromagnet and thereby to the workpiece will transfer a mechanical impulse. The workpiece is thereby brought to move in the direction of the arrow. Then the magnet keeper is brought back by the resilient element 8. The return motion of the magnet keeper is caught by the resilient element 9, working against the stop 6. The resilient elements can consist of coil springs or of bodies of a resilient material, for instance plastic.

According to an essential feature of the present invention the impact of the magnet keeper against one or both of the magnet poles thus will bring about an impulse in the main displacement direction while the retrograde motion of the magnet keeper is caught up softly in order that the impulse in the opposite direction will be small as compared to the first impulse. If the second impulse will result in a displacement of the workpiece in the opposite direction, this will be smaller than the displacement in the main direction, resulting in a net displacement in the main direction. However, it is preferable when practising the present invention that the retrograde motion of the magnet keeper is caught up sufficiently soft so that no retrograde displacement of the workpiece will be caused.

At a preferred embodiment of the present invention the displacement of the workpiece is performed intermittently, i.e. the workpiece is at rest at the moment for the impact, and its displacement caused by the mechanical impulse will come to an end before the retrograde motion of the magnet keeper will be caught up by the resilient element. Then it is required that the impulse generated by the impact of the magnet keeper against one or both of the magnet poles represents a force, sufficiently great to overcome the static friction between workpiece and sliding surface, while the force in the opposite direction when the magnet keeper is caught by the resilient element is sufficiently small, not to overcome this static friction. At this embodiment of the present invention thus the displacement is performed step by step. If the electromagnet is given a voltage pulse the workpiece will perform a displacement of one step. The step length then is depending on the voltage for a coil having a given number of turns of winding and a given resistance. The electromagnet is suitable connected to a voltage source which generates a series of voltage pulses, in which way multiple step displacement easily can be accomplished. It is suitable that the frequency of the voltage pulses is in accordance with the mechanical resonance frequency of the magnet keeper and the resilient element, performing the retrograde motion. As an example of a typical frequency 25 Hz can be mentioned, at which step lengths of $10^{-5} - 10^{-7}$ m easily can be achieved.

The device shown in FIG. 2 functions correspondingly. The arrangement of electromagnet and stop, respectively, in relation to the workpiece has is this embodiment been shifted, while the magnet keeper is moving in the direction from the workpiece, when the electromagnet is given a voltage pulse. The displacement of the workpiece will be in the direction of the arrow.

The device shown in FIG. 3 works similarly. To displace the workpiece in the direction of the arrow, the electromagnet 12 is given a voltage pulse or a series of voltage pulses, respectively. After the impact of the magnet keeper against the magnet poles 1, the retrograde motion of the magnet keeper is caught up by the resilient element 17. At displacement of the workpiece in the opposite direction the electromagnet 14 is instead given a voltage pulse or a series of voltage pulses, respectively. After the impact of the magnet keeper of the magnet poles 15 the retrograde motion of the magnet keeper is caught up by the resilient element 16.

The device shown in FIG. 4 functions correspondingly. When the workpiece should be displaced in the direction of the arrow the first electromagnet 20 is given a voltage pulse. The magnet poles 21 and the magnet casing 19 will then be attracted against the first magnet keeper 24 and hit this one with an impact. At displacement of the workpiece in the opposite direction the electromagnet 22 is instead given a voltage pulse.

It is preferred to be able to displace the workpiece to an arbitrary point in an imagined coordinate system at the sliding surface. Then the workpiece can be provided with devices according to the invention or displacement forwards and backwards along two perpendicular axes. A parallel epipedical workpiece then can be provided on four sides by devices according to FIG. 1 or 2, or on two perpendicular sides with devices according to FIG. 3 or 4.

The device shown in FIG. 5 is intended for such displacement towards and backwards along two perpendicular axes, utilizing one and the same magnet keeper, being of spherical shape, at all displacements. At displacement in the direction of the arrow the electromagnet 31 is given a voltage pulse, whereby the magnet keeper 46 will roll against the magnet poles 35 and 36 and hit the magnet pole 35 with an impact, which will transfer a mechanical impulse to the workpiece. After the impact the magnet keeper is returning and the retrograde motion is caught up softly without impact. At the embodiment shown in the figure this is accomplished by a magnetic field between the magnet poles 44 and 45, generated by the electromagnet 43. It is preferred that this magnet field is kept constant. By giving any of the electromagnets 31, 32, 33, 34 a voltage pulse, thus the workpiece can be displaced in an arbitrary direction.

In the embodiment shown in FIG. 6 the electromagnet is substituted by the piezoelectrical element 49, which, when it is given a voltage pulse, will undergo a shape change, which will give the block 48 a mechanical impulse, which in its turn will be transferred to the workpiece and will bring about the displacement of this one. The block 48 can be suspended at the workpiece by a resilient element 53. Alternatively, the block 48 can be directly attached to the workpiece.

A parallel epipedical workpiece suitably can be provided with devices according to FIG. 6 on four sides for displacement of the workpiece forwards and backwards along two perpendicular axes.

The piezoelectrical element in the embodiment shown in FIG. 6 could also be connected to a voltage source, which generates a series of voltage pulses, whereby multiple steps of displacements easily can be achieved. At this embodiment the frequency range 10,000–50,000 Hz is preferably practised.

It should be appreciated that displacement along for instance a circle arc, i.e. turning movements, should not be regarded as falling outside the scope of the invention. Devices according to the invention then could be situated in the periphery around a turning point having vertical or horizontal axis. If, for instance, in the device according to FIG. 5 the upper surface 54 of the workpiece is forming sliding surface for another workpiece, the motion of which is centered by the circular recess 30 and which is provided with peripherically situated devices according to the invention, displacement to an arbitrary point in an imagined coordinate system as well as to an arbitrary angle can be accomplished.

I claim:

1. Method for displacement of a workpiece in a given direction with respect to a supporting surface, the workpiece slidably resting on said surface and the static coefficient of friction between the workpiece and surface exceeding the dynamic coefficient of friction, said workpiece supporting a body for reciprocatory movement of the body with respect to the workpiece, comprising the steps of imparting an initial force to said body to propel said body from a position at rest toward a second position at a rate of movement sufficient to impart at said second position an impact force to said workpiece to overcome the static coefficient of friction to move said workpiece in said given direction, imparting an opposite reaction force less than said impact force on said body at said second position to move the body to a third position beyond said position at rest and on the side of the position at rest away from said second position, and imparting another opposite reaction force to said body at said third position to return the body to a position at rest.

2. Method of claim 1, which includes the step of imparting another initial force on said body when the body has returned to a position at rest to again move the workpiece in said given direction.

3. Method of claim 1, which includes the step of imparting at least one of said reaction forces by yieldable energy storing means supported by the workpiece.

4. Method of claim 1, which includes the step of imparting at least one of said reaction forces by electromagnetic means supported by the workpiece.

5. Method of claim 1, which includes the steps of imparting both of said reaction forces by yieldable energy storing means supported by the workpiece.

6. Method of claim 1, which includes the steps of imparting both of said reaction forces by electromagnetic means supported by the workpiece.

7. Method of claim 1, which includes the step of imparting said initial force on the body by electromagnetic means supported by the workpiece.

8. Method of claim 7, which includes the step of imparting at least one of said reaction forces by electromagnetic means supported by the workpiece.

9. Method of claim 7, which includes the steps of imparting all of said forces to said body by electromagnetic means supported by said workpiece.

10. Method of claim 9, which includes the steps of imparting at least two of said forces on said body by two electromagnetic means supported by said workpiece at spaced locations.

11. Method of claim 1, which includes the step of imparting said initial force by energizing an expandable magnetostrictive device supported by said workpiece.

12. In a device for displacement in a given direction of a workpiece slidably resting on a supporting surface, the static coefficient of friction between the workpiece and surface exceeding the dynamic coefficient of friction comprising, a body mounted on said workpiece for reciprocatory movement, electrically energized means mounted on said workpiece for inducing movement of said body in one direction from a position at rest to a second position, stop means on said workpiece at said second position to absorb an impact force upon contact with the body to move the workpiece, force imparting means mounted on said workpiece for imparting an opposite reaction force less than said impact force on said body at said second position to move the body to a third position beyond said position at rest and for imparting to the body at the third position another reaction force to return the body to a position at rest.

13. Device as claimed in claim 12, wherein said workpiece includes yieldable energy-storing means supported at one of the second and third positions for imparting one of said reaction forces upon contact with said body.

14. Device as claimed in claim 12, wherein at least one of said reaction forces is imparted by electromagnet means supported by said workpiece.

15. Device as claimed in claim 12, wherein said workpiece includes yieldable energy-storing means supported at both said second and third positions for imparting both of said reaction forces upon respective contact with said body.

16. Device as claimed in claim 12, wherein both of said reaction forces are imparted by electromagnet means supported by said workpiece.

17. Device as claimed in claim 12, wherein said body is magnetic and said initial force is imparted to the body by electromagnetic means supported by said workpiece.

18. Device as claimed in claim 17, wherein at least one of said reaction forces is imparted by electromagnetic means supported by said workpiece.

19. Device as claimed in claim 17, wherein all of said forces are imparted by electromagnetic means supported by said workpiece.

20. Device as claimed in claim 19, wherein said body comprises a ball rolling on a flat surface of said workpiece between all of said positions, and said forces are imparted by electromagnets having pole pieces positioned respectively at said second and third positions.

21. Device as claimed in claim 20, wherein the pole piece positioned at said third position is spaced away from said flat surface at a distance sufficient to avoid physical contact with the rolling ball.

22. Device as claimed in claim 21, wherein said electromagnets include at least two other pole pieces spaced from the pole piece at said third position and spaced from each other to respectively attract said ball away from said third position in angularly related directions.

23. Device as claimed in claim 12, wherein said body comprises a magnetostrictive element connected to said workpiece by resilient mounting means for yielding movement in alignment with said given direction, the magnetostrictive element, when energized, being guided by the mounting means into abutment with the workpiece to impart said impact force, said reaction forces being imparted to the body by said mounting means.

* * * * *